United States Patent [19]

Schürle et al.

[11] Patent Number: 4,703,522
[45] Date of Patent: Nov. 3, 1987

[54] LASER SAFETY EYEGLASSES

[75] Inventors: Hermann Schürle, Aalen; Wolfgang Grimm, Heidenheim; Heinz-Wilhelm Paysan, Aalen-Waldhausen, all of Fed. Rep. of Germany

[73] Assignee: Carl-Zeiss-Stiftung, Heidenheim, Fed. Rep. of Germany

[21] Appl. No.: 922,354

[22] Filed: Oct. 23, 1986

[30] Foreign Application Priority Data

Nov. 16, 1985 [DE] Fed. Rep. of Germany ... 8532493[U]

[51] Int. Cl.$^4$ ............................ A61F 9/02; A61F 9/04
[52] U.S. Cl. ........................................... 2/432; 2/449; 351/44
[58] Field of Search ..................... 2/15, 412, 431, 432, 2/439, 445, 446, 449, 450; 351/44, 46, 158

[56] References Cited

U.S. PATENT DOCUMENTS

| | | | |
|---|---|---|---|
| 1,804,922 | 5/1931 | Feltman et al. | 351/46 |
| 2,932,066 | 4/1960 | Lindblom | 351/44 X |
| 3,384,903 | 5/1968 | Malcom, Jr. | 351/44 X |
| 3,436,761 | 4/1969 | Liautaud et al. | 351/44 X |
| 3,519,339 | 7/1970 | Hutchinson et al. | 351/44 |
| 4,021,862 | 5/1977 | Glasser et al. | 2/431 |
| 4,316,654 | 2/1982 | Allen | 351/158 X |
| 4,547,909 | 10/1985 | Bell | 2/449 X |

FOREIGN PATENT DOCUMENTS

| | | | |
|---|---|---|---|
| 2062829 | 8/1973 | Fed. Rep. of Germany | 351/44 |
| 3116760 | 11/1982 | Fed. Rep. of Germany | 2/431 |

*Primary Examiner*—Wm. Carter Reynolds
*Attorney, Agent, or Firm*—Walter Ottesen

[57] ABSTRACT

Laser safety eyeglasses include two protective filters for protecting the eyes against radiation from a laser. The eyeglasses include a frame having a main body defining two rims for accommodating the respective protective filters therein. Metal shielding plates are attached on the upper side of the frame as well as at the hinge ends of both mounting arms. The shielding plates stretch across the respective free regions between the frame and the face of the user. The mounting rims in which the protective filters are received as well as their connecting bridge are at least partially made of the same metal as the shielding plates.

7 Claims, 3 Drawing Figures

LASER SAFETY EYEGLASSES

FIELD OF THE INVENTION

The invention relates to laser safety eyeglasses which comprise protective filters and a frame for receiving the filters therein.

BACKGROUND OF THE INVENTION

Such safety eyeglasses must be worn when working with laser beams in order to protect the eyes against damaging radiation. They comprise protective filters which substantially absorb the radiation in the wavelength range of the laser utilized and which are usually held in conventional eyeglass frames made of nonmetallic materials.

Such laser safety eyeglasses do protect the eyes of the user from radiation which essentially comes head on and enters through the protective filters. However, these safety eyeglasses do leave regions open between the upper edge of the mounting frame and the eyebrows of the user and between the lateral edges of the mounting frame and the temple. When working with laser beam apparatus, it is quite possible that when the user of such safety eyeglasses drops or rotates the head, laser radiation can gain access to the eye of the user through these unprotected regions causing damage thereto.

SUMMARY OF THE INVENTION

In view of the above, it is an object of the invention to provide laser safety eyeglasses which reliably protect the eyes of the user and indeed in every position of the head. The safety eyeglasses should be so configured that the protection is also guaranteed in the presence of high-intensity laser radiation.

According to a feature of the laser safety eyeglasses of the invention, metal shielding plates are attached on the upper side of the eyeglass frame as well as at the hinge ends of both mounting arms. The shielding plates stretch across the respective free regions between the frame and the face of the user. According to another feature of the invention, the mounting rims in which the protective filters are received as well as their connecting bridge are at least partially made of the same metal as the shielding plates. The metal used must have a good heat conductivity and be easily workable. A metal preferable for this use is sold in the Federal Republic of Germany under the trade name "Neusilber" and is an alloy which comprises copper, zinc and nickel.

The laser safety eyeglasses according to the invention reliably protect the eyes of the user also against high-intensity laser radiation. In addition, the protective filter can not fall out of the frame in response to localized damage to the frame.

In order that the laser safety eyeglasses not be too heavy, it is advantageous to use an eyeglass frame made of nonmetallic material and to cover the side of the frame rims which receive the protective filters as well as the connecting bridge with metal plates on the side thereof facing toward the laser radiation. The metal plates consist of a metal having a good heat conductivity. The shielding plates on the upper end of the frame and on the forward arm ends are preferably made of the same metal and have the same thickness as the cover plate of the frame rims.

The cover plate can be so configured that it covers over only the upper portion of the rims of the frame. The cover plate extends downwardly in the regions of the lateral edges of the frame at the temples just as far down as the shielding plates attached to the arms. This prevents the protective filters from falling out in the event of damage to the non-protected lower portion of the frame rims.

The outer surfaces of the shielding and cover plates are configured so as to be diffusedly reflecting such as with brushing of the surface. This prevents an intense radiation beam from being mirror-reflected and from permitting the reflected beam to cause possible damage. At the same time, such a configuration of the metal parts substantially improves the esthetic impression presented by the frame.

BRIEF DESCRIPTION OF THE DRAWING

The invention will now be described with reference to the drawing wherein.

DESCRIPTION OF THE PREFERRED EMBODIMENTS OF THE INVENTION

Figure 1:
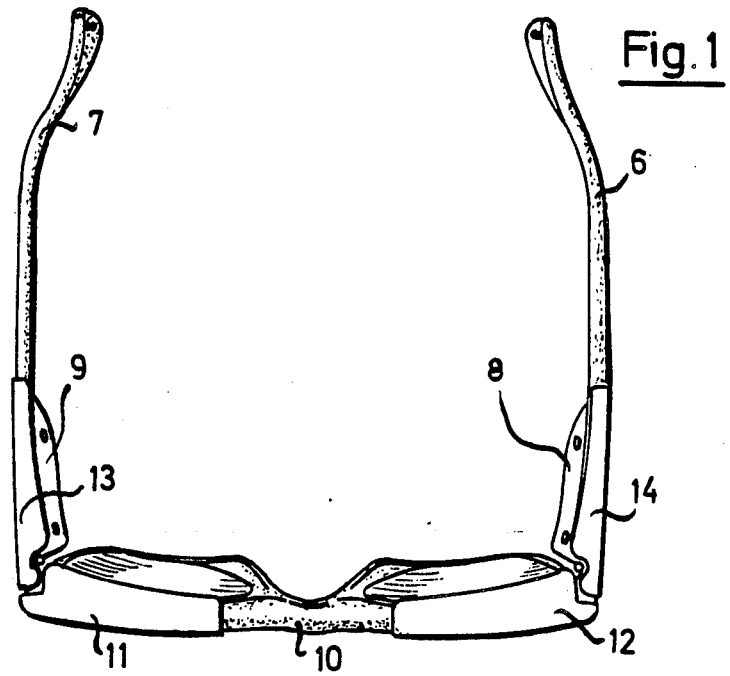
FIG. 1 is a plan view of the laser safety eyeglasses according to the invention.
Figure 2:
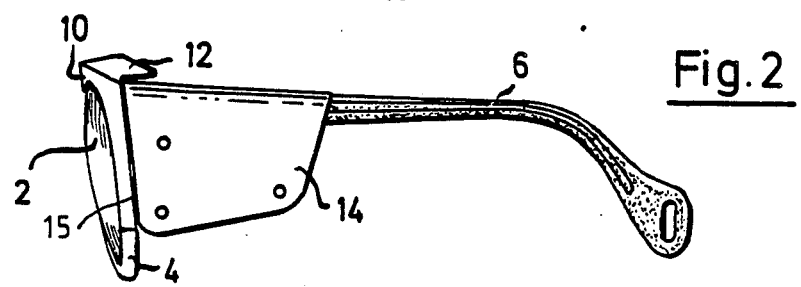
FIG. 2 is a side elevation view of the safety eyeglasses shown in FIG. 1.
Figure 3:
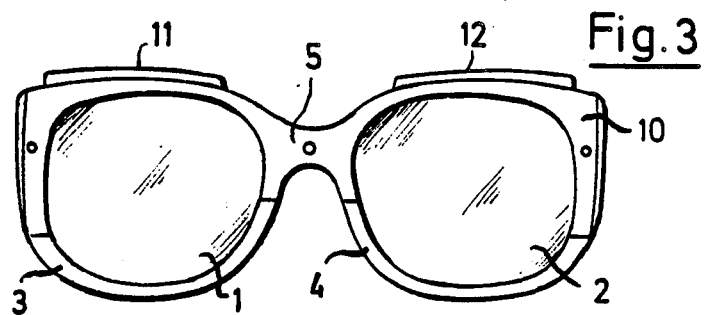
FIG. 3 is a front elevation view of the safety eyeglasses of FIG. 1.

In the embodiments shown in FIGS. 1 to 3, a frame of nonmetallic material is utilized which is configured as the frame of working eyeglasses and which is approved for such use. This frame includes two frame rims for receiving and accommodating the laser protective glasses 1 and 2. The frame further includes a connecting bridge 5 for interconnecting the rims 3 and 4. On the lateral outside edges of the frame rims, arms 6 and 7 are connected by means of hinges. The hinge ends of the arms 6 and 7 are provided with plastic plates 8 and 9, respectively, which cover over the regions between the outside edges of the rims and the temples of the user.

In order to provide the laser safety eyeglasses, this eyeglass frame is configured as will now be described below.

The upper part of the rims 3, 4 and the connecting bridge 5 are clad or covered with a plate 10 made of good heat conductive metal such as the "Neusilber" referred to above. The plate 10 is preferably configured as a unitary piece and bent downwardly toward the rear at the upper edge of the frame parts 3 and 4. This plate 10 defines the shielding plates 11 and 12 which extend over the region between the frame and the eyebrows of the user when worn by the latter. The cover plate 10 extends over the frame rims 3 and 4 also laterally in the region of the temples.

The shielding plates 13 and 14 are attached to the hinged ends of the arms 6 and 7; these shielding plates 13 and 14 extend over the region between the frame rims 3 and 4 and the temple of the user when the eyeglasses are worn by the latter.

The shielding plates 13 and 14 are made of the same material as the shielding plate 10 and have the same thickness, for example, 0.5 mm. The outer surface of these plates is configured so as to be diffusely reflectant. As shown in FIGS. 2 and 3, the shielding plate 10 extends downwardly at lateral edges 15 in the region of the temples just as far as the shielding plates 13 and 14 connected to the arms 6 and 7, respectively. In this way, it is assured that even with damage to the nonprotected parts of the frame rims 3, 4, the protective filters 1 and 2 cannot fall out of the frame.

The protective filters 1 and 2 can be configured with or without an optical effect. The frame rims 3 and 4 are so configured that the protective filters 1 and 2 can be positioned from the front of the eyeglasses, that is, from the side thereof facing toward the laser radiation.

The laser protective eyeglasses shown in FIGS. 1 to 3 reliably protect the user when working with Nd-YAG-lasers and with $CO_2$ lasers when the protective filters 1 and 2 are appropriately configured and fulfill the requirements of the German industrial standard 58 215 (DIN 58 215).

As shown in FIGS. 1 to 3, the esthetic appearance of the laser safety eyeglasses according to the invention corresponds substantially to the appearance of working protective eyeglasses which are in general use.

It is understood that the foregoing description is that of the preferred embodiments of the invention and that various changes and modifications may be made thereto without departing from the spirit and scope of the invention as defined in the appended claims.

What is claimed is:

1. Laser safety eyeglasses comprising:
   two protective filters for protecting the eyes against radiation from a laser;
   a frame having a main body defining two holders for accommodating said protective filters, respectively, and having two arms hinge connected to said main body, said main body including a bridge for interconnecting said holders and having an upper edge and an outer face facing away from the wearer; said holders being annular members having respective upper portions;
   a plurality of shielding plates made of a predetermined metal for shielding the wearer of the eyeglasses from laser radiation, a first two of said shielding plates being mounted on corresponding ones of said arms at the ends thereof connected to said main body so as to cover over the region between said frame and the face of the wearer, and a second two of said shielding plates being mounted on said upper edge above corresponding ones of said holders and extending inwardly toward the face of the wearer so as to cover over the region between said frame and the face of the wearer; and,
   shielding metal means for covering at least said outer face at said upper portions and said bridge, said shielding metal means being made of a metal plate having a good heat conductivity.

2. The laser safety eyeglasses of claim 1, wherein said frame is made of a non-metal material and said shielding metal means covering only said upper portions and said bridge.

3. The laser safety eyeglasses of claim 1, said metal plate and said second two shielding plates being a single integral piece.

4. Laser safety eyeglasses comprising:
   two protective filters for protecting the eyes against radiation from a laser;
   a frame having a main body defining two holders for accommodating said protective filters, respectively, and having two arms hinge connected to said main body, said main body having an upper edge;
   a plurality of shielding plates made of a predetermined metal for shielding the wearer of the eyeglasses from laser radiation, a first two of said shielding plates being mounted on corresponding ones of said arms at the ends thereof connected to said main body so as to cover over the region between said frame and the face of the wearer, and a second two of said shielding plates being mounted on said upper edge above corresponding ones of said holders and extending inwardly toward the face of the wearer so as to cover over the region between said frame and the face of the wearer;
   said main body including a bridge for interconnecting said holders, said holders and said bridge being made at least partially of said metal;
   said frame being made of a non-metal material and having an outer face away from the wearer;
   sheet metal means for covering said outer face at said holders and said bridge, said sheet metal means being made of a metal having a good heat conductivity; and,
   said holders being annular members having respective upper portions and said sheet metal means being a metal plate covering only said upper portions and said bridge.

5. The safety glasses of claim 4, said annular members having respective lateral edges adjacent the respective temples of the wearer, said metal plate extending downwardly at said lateral edges as far as said first two of said shielding plates.

6. The laser safety eyeglasses of claim 5, said metal plate being configured to extend about and enclose said lateral edges.

7. The laser safety eyeglasses of claim 4, said metal plate and said second two shielding plates being a single integral piece.

* * * * *

UNITED STATES PATENT AND TRADEMARK OFFICE
CERTIFICATE OF CORRECTION

PATENT NO. : 4,703,522

DATED : November 3, 1987

INVENTOR(S) : Hermann Schürle et al

It is certified that error appears in the above-identified patent and that said Letters Patent is hereby corrected as shown below:

In column 4, line 32: after "face" please insert -- facing --.

Signed and Sealed this

Fifteenth Day of March, 1988

Attest:

DONALD J. QUIGG

*Attesting Officer*    *Commissioner of Patents and Trademarks*